(12) United States Patent
Bodenhamer et al.

(10) Patent No.: US 6,692,973 B1
(45) Date of Patent: Feb. 17, 2004

(54) SURFACE BINDING OF AN IMMUNOGLOBULIN TO A FLEXIBLE POLYMER USING A WATER SOLUBLE VARNISH MATRIX

(75) Inventors: William T. Bodenhamer, Jupiter, FL (US); George Jackowski, Kettleby (CA); Eric Davies, Mississauga (CA)

(73) Assignee: Toxin Alert, Inc., Ontario (CA)

( * ) Notice: Subject to any disclaimer, the term of this patent is extended or adjusted under 35 U.S.C. 154(b) by 416 days.

(21) Appl. No.: 09/724,438

(22) Filed: Nov. 28, 2000

Related U.S. Application Data

(63) Continuation-in-part of application No. 09/550,777, filed on Apr. 17, 2000, now Pat. No. 6,376,204, and a continuation-in-part of application No. 09/550,779, filed on Apr. 17, 2000, now Pat. No. 6,379,908, which is a continuation-in-part of application No. 09/218,827, filed on Dec. 22, 1998, now Pat. No. 6,051,388.

(51) Int. Cl.$^7$ ............................................... G01N 33/543
(52) U.S. Cl. ........................... 436/518; 422/55; 422/57; 422/58; 435/6; 435/7.2; 435/7.32; 435/287.1; 435/287.2; 435/287.9; 435/810; 435/970; 436/528; 436/531; 436/535; 436/810; 436/827
(58) Field of Search ............................... 422/55, 57, 58; 435/6, 7.2, 7.32, 287.1, 287.2, 287.9, 810, 970; 436/518, 528, 531, 535, 810, 827

(56) References Cited

U.S. PATENT DOCUMENTS

| | | |
|---|---|---|
| 2,485,566 A | 10/1949 | Clark |
| 3,067,015 A | 12/1962 | Lawdermilt |
| 4,285,697 A | 8/1981 | Neary |
| 4,746,616 A | 5/1988 | Honigs et al. |
| 4,870,005 A | 9/1989 | Akiyoshi et al. |
| 4,966,856 A | 10/1990 | Tsukasa et al. |
| 5,053,339 A | 10/1991 | Patel |
| 5,306,466 A | 4/1994 | Goldsmith |
| 5,869,341 A | 2/1999 | Woodaman |
| 5,942,444 A * | 8/1999 | Rittenburg et al. ......... 436/518 |
| 6,020,047 A | 2/2000 | Everhart |
| 6,051,388 A | 4/2000 | Bodenhamer |

FOREIGN PATENT DOCUMENTS

| | | |
|---|---|---|
| EP | 0699304 B1 | 12/1999 |
| WO | WO 94/27144 | 11/1994 |

* cited by examiner

*Primary Examiner*—Christopher L. Chin
(74) *Attorney, Agent, or Firm*—McHale & Slavin, P.A.

(57) ABSTRACT

The present invention relates to bioassay materials useful for the detection of toxic substances and, more particularly, to packaging materials for food and other products, along with methods for their manufacture and use. The invention provides a unique composite material capable of detecting and identifying multiple biological materials within a single package. The biological material identification system is designed for incorporation into existing types of flexible packaging material such as polyvinylchloride or polyolefin films, and its introduction into the existing packaging infrastructure will require little or no change to present systems or procedures.

8 Claims, 1 Drawing Sheet

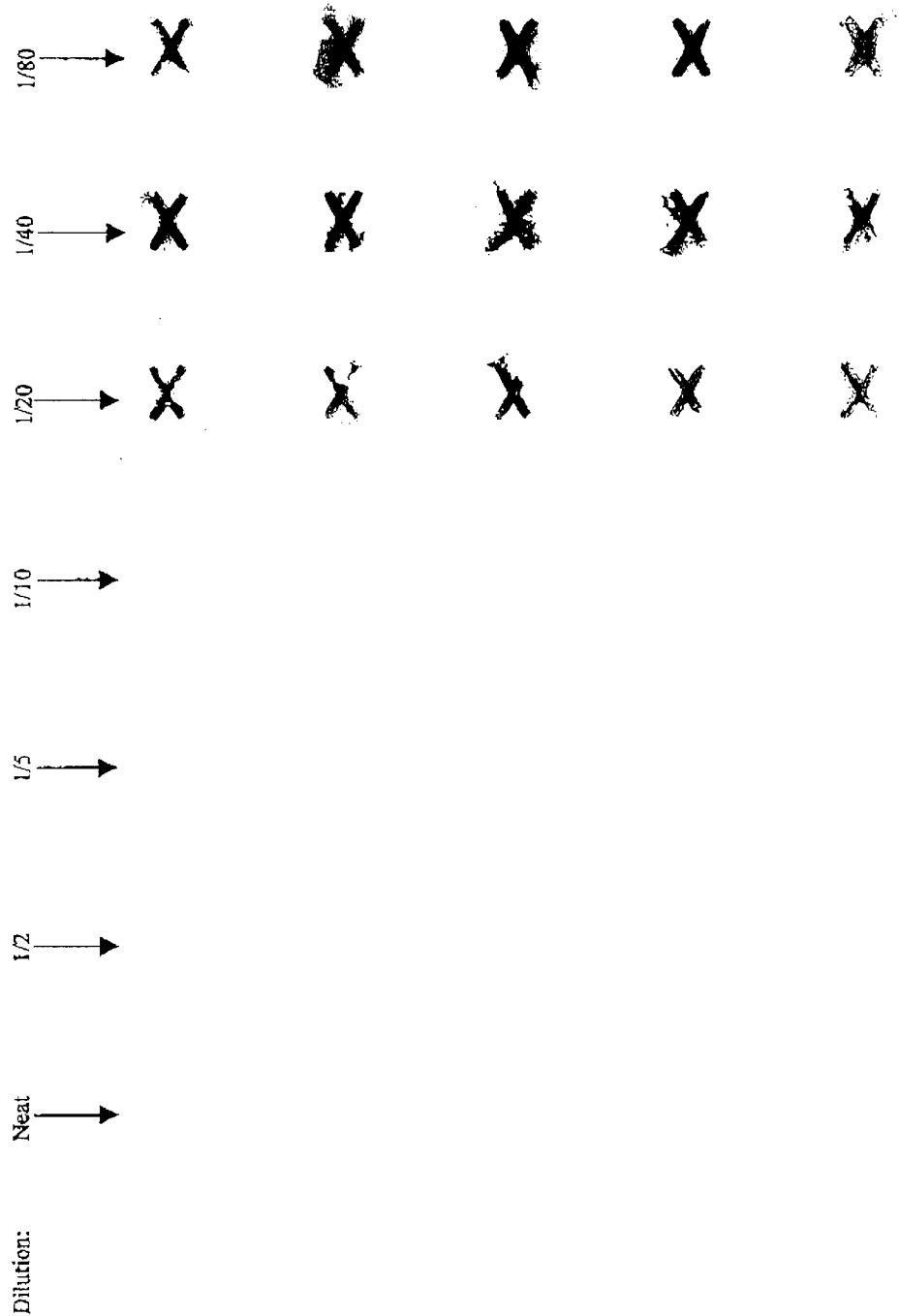

SURFACE BINDING OF AN IMMUNOGLOBULIN TO A FLEXIBLE POLYMER USING A WATER SOLUBLE VARNISH MATRIX

REFERENCE TO RELATED APPLICATIONS

This application is a continuation-in-part of Ser. No. 09/550,777, filed Apr. 17, 2000, now U.S. Pat. No. 6,376,204, having an issue date of Apr. 23, 2002 and Ser. No. 09/550,779, filed Apr. 17, 2000, now U.S. Pat. No. 6,379,908, having an issue date of Apr. 30, 2002, each of which are continuations-in-part of Ser. No. 09/218,827, filed on Dec. 22, 1998, now U.S. Pat. No. 6,051,388, having an issue date of Apr. 18, 2000, the contents of which are all herein incorporated by reference.

FIELD OF THE INVENTION

This invention relates to a method for the attachment of a biologically active material, e.g. ligands or immunoglobulins to the surface of flexible polymer substrate, and to a method for maintaining the biological activity of the attached biologically active materials by utilizing a water gloss overprint varnish matrix.

BACKGROUND OF THE INVENTION

Although considerable effort and expense have been put forth in an effort to control food and/or airborne pathogenic microorganisms, there nevertheless exist significant safety problems in the supply of packaged food and in the certification of sterility for medically useful components, e.g. surgical tools, internal examination devices, e.g. endoscopes, and the like.

For example, numerous outbreaks of food poisoning brought about by foodstuffs contaminated with strains of the *E-Coli*, Campylobacter, Listeria, Cyclospora and Salmonella microorganisms have caused illness and even death, not to mention a tremendous loss of revenue for food producers. These and other microorganisms can inadvertently taint food, even when reasonably careful food handling procedures are followed. The possibility of accidental contamination, for example by temperature abuse, in and of itself, is enough to warrant incorporation of safe and effective biological material diagnosis and detection procedures. Further complicating the situation is the very real possibility that a terrorist organization might target either the food or water supply of a municipality or even a nation itself, by attempting to include a pathogenic microorganism or toxic contaminant capable of causing widespread illness or even death. If, by accident or design, the food supply of a particular population were to be contaminated, it is not only imperative that the population be alerted to the contamination, but it is further necessary that the particular contaminant be quickly and precisely pinpointed so that appropriate countermeasures may be taken.

With respect to medical or dental procedures, there exists a very real possibility for transmission of disease due to ineffective sterilization techniques or careless handling of medical implements, which can often lead to contamination of the sterile field. Although these devices are generally wrapped after sterilization, it is impossible to verify the efficacy of the sterilizing process or determine if subsequent contamination has occurred prior to use.

Thus, if it were possible to readily substitute standard packaging materials with a flexible material capable of 1) quickly and easily detecting the presence, and 2) indicating the particular identity of a variety of pathogenic biological materials, a long felt need would be satisfied.

DESCRIPTION OF THE PRIOR ART

U.S. Pat. No. 6,051,388 discloses bioassay materials which may take the form of packaging materials for food or other products and which are useful for detecting toxic substances The biological assay therein disclosed broadly encompasses a base layer which is a flexible polyolefin film having a surface which has undergone a treatment step effective to enhance the film's ability to immobilize a ligand which has been applied thereto and a biologically active ligand which is immobilized to the film subsequent to which a protectant layer in the form of a gel coat or liquid film is applied. This patent requires separate deposition of the active ligand followed by application of the protectant layer.

U.S. Pat. No. 4,966,856 discloses an analytical element having a layer for antibody/antigen binding but fails to teach or suggest a flexible polyolefin matrix.

U.S. Pat. No. 4,870,005 teaches a multi-layer analysis element including a membrane filter to which an antigen or antibody is immobilized. The concept of forming a flexible analysis element having immobilized biological agents bound thereto is neither suggested nor disclosed.

U.S. Pat. No. 6,020,047 discloses a polymer film coated with a metal alloy and containing a self-assembling monolayer printed on the polymer film.

The prior art fails to teach a single step methodology wherein a composition functions as a carrier or vehicle for purposes of application of a biologically active ligand or the like to the surface of the flexible polymer while simultaneously acting as a viable matrix for maintaining the biological activity of said material.

SUMMARY OF THE INVENTION

The present invention relates to packaging materials for food, medical devices and the like products wherein the presence of pathogenic microorganisms is undesirable, along with methods for their manufacture and use. The presence of undesirable biological materials in the packaged material is readily ascertained by the consumer, merchant, regulator, etc. under ordinary conditions and without the use of special equipment. A multiplicity of biological materials threaten our food supply. The present invention provides a unique composite material capable of detecting and identifying multiple biological materials within a single package. The biological material identification system is designed for incorporation into existing types of flexible packaging material such as polyvinyl chloride and polyolefin films, and its introduction into the existing packaging infrastructure will require little or no change to present systems or procedures. Thus, the widespread inclusion of the biological material detecting system of the instant invention will be both efficient and economical.

In one embodiment of the invention the biological material detecting system prints a pattern containing several of the biologically active agents, e.g. antibodies or aptamers onto a flexible material which is usually a type of polymeric film, preferably a polyvinyl chloride or polyolefin film and most preferably a polyethylene film which has undergone a surface treatment, e.g. corona discharge to further enhance the film's ability to immobilize the antibodies upon its surface.

Each biological agent, for example an antibody, can be tailored so as to be specific to a particular biological material and may be printed upon the flexible substrate in a distinctive icon shape. The detection system may contain any number of biological agents capable of detecting a variety of common toxic microbes; although any number of microbes may be identified via the inventive concept taught herein, for the purpose of this description, the microbes of interest will be limited to E. Coli, Salmonella, Listeria and Cyclospora.

The biological material detecting system will not merely detect the presence of biological materials, it will also identify the particular biological materials located in a packaged product. This unique feature allows for the immediate identification of each particular biological material present since the antibodies are specific to a detector having a definitive icon shape or other identifying characteristic. Although the end use consumer is primarily interested in whether a food product is, or is not, contaminated per se, the ability to detect and identify the particular biological material immediately is of immeasurable value to merchants, processors, regulators and health officials. The ability to immediately identify a toxic material will lead to greatly reduced response times to health threats that might be caused by the biological material and will also enhance the ability for authorities to locate the source of the problem. One means of providing enhanced sensitization is by including a scavenger antibody, which is a biologically active ligand characterized as having a higher affinity for the particular toxic substance than the capture antibody. The scavenger antibody is provide, e.g. by mixing said scavenger body with the combined capture antibody/water gloss overprint varnish, in a sufficient amount to bind with the particular toxic substance up to and including a specific threshold concentration. In this manner, the capture antibody will be prevented from binding with a detector antibody until the concentration of the. particular biological material surpasses the specific threshold concentration. In this manner, the biological material detecting system visually reports only those instances where concentration levels are deemed harmful by health regulatory bodies.

The biological material detecting system of the present invention exhibits an active shelf life in excess of 1 year under normal operating conditions. This enhances the use of a biological material detection system on products which are intended to be stored for long periods of time. If these products are stored so as to be ready for immediate use in some time of emergency, then it is extremely beneficial to definitely be able to determine the safety of the product at the time that it is to be used.

The method of production of the biological material detecting system is designed to be easily incorporated within the packaging infrastructure of existing systems without disruption of the systems or the procedures under which they are operating. The biological material detecting system can be incorporated onto packaging films which are produced by the packager, or those which are supplied by a film manufacturer. The apparatus necessary for applying the biological material detecting system may be easily located within any continuous process such as printing or laminating and will operate as an integral part of an existing system.

The biological material detecting system of the instant invention represents an entirely new packaging material which is designed to inform the consumer of the presence of certain biological materials or pathogens present in food stuffs or other materials packaged within the detecting system. The system is designed so that the presence of a biological material is presented to the consumer in a distinct, unmistakable manner which is easily visible to the naked eye.

An important feature of the biological material detection system is its all-encompassing presence around and upon the product being packaged. Since the biological material detecting system is designed as an integral part of 100% of the packaging material and covers all surfaces as utilized, there is no part of the packaged product which can be exposed to undetected microbes. In the past, the use of single location or in situ detectors have left a majority of the area around and upon the packaged product exposed to undetected microbes. This greatly increased the chance that a spoiled or tainted product might be inadvertently consumed before the toxic agent had spread to the location of the in situ detector. The biological material detection system of the present invention avoids this problem by providing a plurality of individual detectors per unit area which are effective to insure positive detection of any pathogenic microorganisms within the product being tested.

The present inventors have now discovered a method of printing which utilizes a type of Water Gloss FDA Overprint Varnish, e.g. (WVGOO 1006, available from Water Ink Technologies) as a matrix. These varnishes are commercially available and commonly used in the food industry. The product meets the requirements of Federal Register 21 CFR regarding polymeric coatings (Part 175.300) and components of paper and paperboard in contact with dry food (Parts 176.170 & 176.180).

It is an objective of the, present invention to provide a biological material detecting system for protecting the consumer by detecting and unmistakably presenting to the untrained eye visual icons on the packaging material which signify the presence of a number of pathogens in the food stuff or other materials which are at a level harmful to humans.

It is another objective of the instant invention to provide a bioassay material wherein an antigen detecting antibody system is immobilized within a biological activity maintaining varnish matrix upon the surface of a flexible polymer.

It is still another objective of the instant invention to provide a bioassay material wherein an antigen detecting antibody system is immobilized upon the surface of a flexible polymer film.

It is a further objective of the invention to provide a biological material detecting system which is so similar in appearance and utilization that its use, in lieu of packaging materials, is not apparent to the food processor or other packagers.

A still further objective of the present invention is to provide a biological material detecting system which is cost effective when compared to traditional packaging materials.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 1 illustrates the visual result generated in the Example.

DETAILED DESCRIPTION OF THE INVENTION

The instant invention teaches the provision of a bioassay material and methods for its production and use which immobilizes the antibodies onto the surface of a flexible polyvinyl chloride or polyolefin, e.g. a polyethylene, a surface treated polyethylene, a polypropylene, a surface treated polypropylene or mixture thereof.

The particular toxic substance may be one or more members selected from the group consisting of a particular microorganism, biological materials containing the genetic characteristics of said particular microorganism, and mutations thereof. In a particular embodiment, the toxic substance is selected from the group consisting of microorganisms, nucleic acids, proteins, integral components of microorganisms and combinations thereof.

It should also be understood that the invention will function by direct measurement of microbes with certain types of antibodies, selected from the group consisting of an antibody, a single stranded nucleic acid probe, an aptamer, a lipid, a natural receptor, a lectin, a carbohydrate and a protein. The biological materials may also be measured by non-immunological methods in particular using labeled molecules, such as aptamers, which have a high affinity for the biological materials.

The invention utilizes various types of detector antibodies, e.g. those conjugated with dyes to produce a visual cue, or alternatively, photoactive compounds capable of producing a visual cue in response to a particular type of light exposure, for example a scanning system which detects luminescent properties which are visualized upon binding of the antigen and antibody. In this method of construction biological materials are measured directly with a biologically active ligand, e.g. an antibody, aptamer, nucleic acid probe or the like, which induces a conformational change to produce a visual cue.

It is also understood that specific polymers may be incorporated into the invention and that when a biological material is bound to the surface it induces a molecular change in the polymer resulting in a distinctly colored icon.

The inventor has now discovered that it is possible to attach biologically active ligands to the surface of various flexible polymers, for example polyvinyl chloride and polyolefins, e.g. a polyolefin sheet having appropriate properties of transparency and flexibility and that the composite functions as a biological sensor or assay material. These films may be untreated polyethylene or polyvinyl chloride films which are amenable to antibody immobilization by various mechanisms, e.g. by adsorption. In a particular embodiment, the films may be first cleaned, e.g. by ultrasonication in an appropriate solvent, and subsequently dried. For example the polymer sheet may be exposed to a fifteen minute ultrasonic treatment in a solvent such as methylene chloride, acetone, distilled water, or the like. In some cases, a series of solvent treatments are performed. Subsequently the film is placed in a desiccating device and dried. Alternatively, these films may be created by first exposing the film to an electron discharge treatment at the surface thereof, then printing with a fluorescing antibody receptor. Subsequently, a drying or heating step may be utilized to treat the film to immobilize the receptor.

Additional modifications to polyolefin films may be conducted to create the presence of functional groups, for example a polyethylene sheet may be halogenated by a free radical substitution mechanism, e.g. bromination, chlorosulfonation, chlorophosphorylation or the like. Furthermore, a halodialkylammonium salt in a sulfuric acid solution may be useful as a halogenating agent when enhanced surface selectivity is desirable.

Grafting techniques are also contemplated wherein hydrogen abstraction by transient free radicals or free radical equivalents generated in the vapor or gas phase is conducted. Grafting by various alternative means such as irradiation, various means of surface modification, polyolefin oxidation, acid etching, inclusion of chemical additive compounds to the polymer formulation which have the ability to modify the surface characteristics thereof, or equivalent techniques are all contemplated by this invention.

Additionally, the formation of oxygenated surface groups such as hydroxyl, carbonyl and carboxyl groups via a flame treatment surface modification technique is contemplated.

Further, functionalization without chain scission by carbene insertion chemistry is also contemplated as a means of polymer modification.

Illustrative of the types of commercially available films which might be utilized are polyvinyl chloride films and a straight polyethylene film with electron discharge treatment marketed under the trademark SCLAIR®. The electron discharge treatment, when utilized, renders the film much more susceptible to immobilization of the antibodies on its surface. Additional films which might be utilized are Nylon 66 films, for example DARTEK®, a coextrudable adhesive film such as BYNEL® and a blend of BYNEL® with polyethylene film.

The invention will be further illustrated by way of the following example:

1. Water Gloss FDA Overprint Varnish WVGOO1006 was diluted with UHF pure water to final concentrations of 1:2. 1:5, 1:10, 1:20, 1:40, and 1:80.

The varnish has the properties of being grease resistant, heat resistant to 175° F., 30 PSI, 2 sec. dwell, Krome Kote, face to paper; COF 25°–30° F., clear, glossy finish, non-scuff resistant, not imprintable, viscosity/CPS 20–25 sec, #3 Zahn at 77° F., pH 9.2–9.6.

2. A monoclonal anti-Listeria monocytogenes capture immunoglobulin (MAb 833) was added to each dilution of the varnish, including one aliquot of neat (undiluted) varnish, for a final concentration of 20 ug/mL in each sample.

3. A sheet of corona discharge treated PE was placed between two pieces of acrylic, of which the uppermost component served as a template. The template possessed 7 columns of 5 bottomless X shaped wells in which samples could be applied directly to the surface of the PE. The two acrylic components were secured by a series of clamps and bolts to prevent leakage.

4. 10 $\mu$L of the undiluted varnish, containing 200 ng of immunoglobulin, was applied to each well of column 1. The procedure was repeated sequentially for the 6 varnish dilutions, beginning with the 1:2 dilution added to each of the 5 wells of column 2.

5. Samples were allowed to air dry at room temperature for 1 hour.

6. A second horseradish peroxidase (HRP) conjugated monoclonal anti-Listeria monocytogenes antibody (MAb 832) was diluted to a 1:4000 concentration in phosphate buffered saline (PBS), pH 7.4.

7. Heat killed Listeria-monocytogenes cells (antigen) were added to the HRP conjugate solution at a concentration of $10^5$ cells per mL.

8. 100 $\mu$L of the antigen/conjugate solution, representing 10,000 Listeria monocytogenes cells, was added to each well of the template and allowed to incubate for 1 hour at room temperature.

9. The template was disassembled and the sheet of PE washed briefly with UHF water to remove any excess conjugate.

10. The polyethylene sheet was placed in a 50 mL bath of TMB substrate for peroxidase (available from Vector Laboratories).

11. Color development was allowed to continue for 15 minutes prior to removing the PE sheet from the substrate bath. The reaction was stopped by rinsing the PE sheet with UHF water.

Results

1. No color development was observed in columns 1–4.
2. Distinct color development was observed in each well of columns 5–7.
3. Color could not be removed by the application and subsequent lifting of adhesive tape.

Color development indicates that the biological activity of the capture antibody applied to the PE surface is not adversely affected by Water Gloss FDA Overprint Varnish WVG001006. Alternatively, the absence of color development in columns 1–4 (neat-1:10 dilutions) indicates that a threshold exists in the concentration of varnish applied to the polyethylene surface. Binding is thus inhibited at concentrations lower than 1:20. Furthermore, the inability to remove color from the PE surface using adhesive tape indicates that binding of the immunoglobulin to the PE surface is stable and that leaching from the PE surface over time will not occur.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A biological assay material for detecting the presence of a particular toxic substance comprising:
    a base layer which is a flexible polymer;
    a first biologically active ligand characterized by its ability to recognize an epitope of the particular toxic substance; and
    a water gloss overprint varnish;
    wherein said water gloss overprint varnish provides a biological activity maintaining matrix which immobilizes said first biologically active ligand upon a surface of said base layer.

2. The biological assay material according to claim 1 wherein:
    said base layer has a surface which has undergone a treatment step effective to enhance said polymer's ability to immobilize a ligand applied thereto.

3. The biological assay material according to claim 1 wherein:
    the flexible polymer is selected from the group consisting of polyvinylchloride, polyethylene, polypropylene and mixtures thereof.

4. The biological assay material according to claim 1 wherein:
    said base layer is surface treated by a corona discharge process.

5. The biological assay material according to claim 1 wherein:
    the particular toxic substance is one or more members selected from the group consisting of a particular microorganism, biological materials containing the genetic characteristics of said particular microorganism, and any mutations thereof.

6. The biological assay material according to claim 1 wherein:
    the particular toxic substance is selected from the group consisting of microorganisms, nucleic acids, proteins, integral components of microorganisms and combinations thereof.

7. The biological assay material according to claim 1 wherein said first biologically active ligand is selected from the group consisting of an antibody, a single stranded nucleic acid probe, an aptamer, a lipid, a natural receptor, a lectin, a carbohydrate and a protein.

8. The biological assay material according to claim 1 further including:
    a scavenger antibody which is a second biologically active ligand characterized as having a higher affinity for the particular toxic substance than said first biologically active ligand, said scavenger antibody being combined with said first biologically active ligand and water gloss overprint varnish in a sufficient amount to bind with the particular toxic substance up to and including a specific threshold concentration;
    whereby said first biologically active ligand will be prevented from binding with a detector antibody until the concentration of the particular toxic substance surpasses the specific threshold concentration.

* * * * *